United States Patent
Zhang et al.

(10) Patent No.: US 6,340,749 B1
(45) Date of Patent: *Jan. 22, 2002

(54) PREPARATION OF NUCLEOSIDE PHOSPHORAMIDITES AND OLIGONUCLEOTIDE SYNTHESIS

(75) Inventors: Zhaoda Zhang; Jin-Yan Tang, both of Shrewsbury, MA (US)

(73) Assignee: Avecia Biotechnology Inc., Milford, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/647,354

(22) Filed: May 9, 1996

Related U.S. Application Data

(63) Continuation-in-part of application No. 08/539,939, filed on Oct. 6, 1995.

(51) Int. Cl.$^7$ ................................................ C07H 21/00
(52) U.S. Cl. ................ 536/25.34; 536/25.32; 536/25.3; 548/111
(58) Field of Search ............................. 536/25.32, 25.3, 536/25.34; 548/111

(56) References Cited

U.S. PATENT DOCUMENTS 4,474,948 A * 10/1984 Hudson et al. ............... 536/27

OTHER PUBLICATIONS

Zhang et al. (1996) *Tetrahedron Letters* 37:331–334.
Moore et al. (1985) *J. Org. Chem.* 50:2019–2025.

* cited by examiner

*Primary Examiner*—Gary Geist
*Assistant Examiner*—Howard V. Owens
(74) *Attorney, Agent, or Firm*—Hamilton, Brook, Smith & Reynolds, P.C.

(57) ABSTRACT

The invention provides novel bifunctional phosphitylating reagents and their application in in situ preparation of 5'-protected nucleoside phosphoramidites and synthesis of oligonucleotides. Bifunctional phosphitylating reagents according to the invention react quickly with nucleosides under neutral or weakly basic conditions, without an additional activation step. In addition, the bifunctional phosphitylating reagents according to the invention generate chemoselectively the corresponding nucleoside phosphoramidites in situ, without need to purify the nucleoside phosphoramidites before using them in oligonucleotide synthesis. Finally, the bifunctional phosphitylating reagents according to the invention are relatively stable and easy to handle.

6 Claims, 4 Drawing Sheets

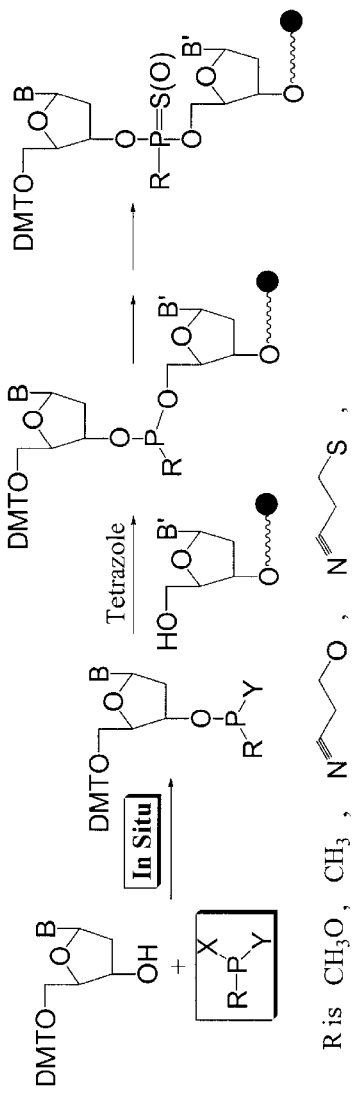
Figure 2
R is CH₃O, CH₃, 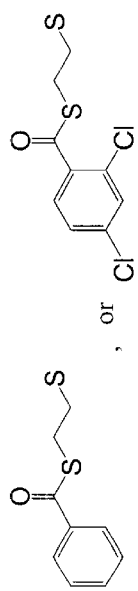,
wherein the right-most O, C, or S is the point of attachment to phosphorous;
X is 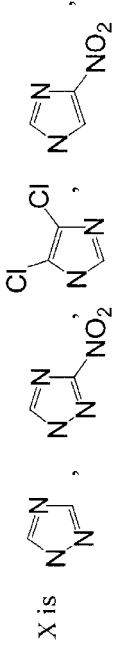,
wherein the left-most N is the point of attachment to phosphorous;
and Y is 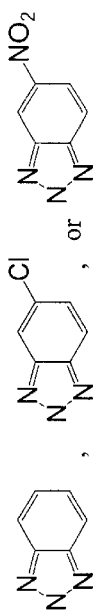, 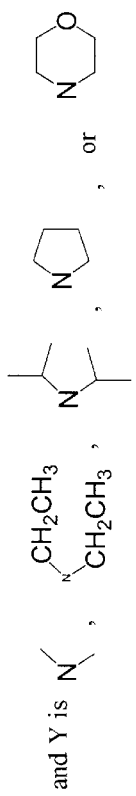
wherein the left-most N is the point of attachment to phosphorous.

PREPARATION OF NUCLEOSIDE PHOSPHORAMIDITES AND OLIGONUCLEOTIDE SYNTHESIS

This is a continuation-in-part of U.S. Ser. No. 08/539,939, filed Oct. 6, 1995.

BACKGROUND OF THE INVENTION

1. Field of the Invention

The invention relates to the chemical synthesis of oligonucleotides and to chemical entities useful in such synthesis.

2. Summary of the Related Art

Oligonucleotides have become indispensable tools in modern molecular biology, being used in a wide variety of techniques, ranging from diagnostic probing methods to PCR to antisense inhibition of gene expression. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See e.g., *Methods in Molecular Biology. Vol 20: Protocols for Oligonucleotides and Analogs* pp. 165–189 (S. Agrawal, Ed., Humana Press, 1993); *Oligonucleotides and Analogues: A Practical Approach*, pp. 87–108 (F. Eckstein, Ed., 1991); and Uhlmann and Peyman, supra. Agrawal and Iyer, Curr. Op. in Biotech. 6: 12 (1995); and Antisense Research and Applications (Crooke and Lebleu, Eds., CRC Press, Boca Raton, 1993). Early synthetic approaches included phosphodiester and phosphotriester chemistries. Khorana et al., J. Molec. Biol. 72: 209 (1972) discloses phosphodiester chemistry for oligonucleotide synthesis. Reese, Tetrahedron Lett. 34: 3143–3179 (1978), discloses phosphotriester chemistry for synthesis of oligonucleotides and polynucleotides. These early approaches have largely given way to the more efficient phosphoramidite and H-phosphonate approaches to synthesis. Of these, the phosphoramidite approach has become the most popular for most applications. Beaucage and Caruthers, Tetrahedron Lett. 22: 1859–1862 (1981), discloses the use of deoxynucleoside phosphoramidites in polynucleotide synthesis. The phosphoramidite approach has been used to synthesize oligonucleotides having a variety of modified internucleoside linkages. Agrawal and Goodchild, Tetrahedron Lett. 28: 3539–3542 (1987), teaches synthesis of oligonucleotide methylphosphonates using phosphoramidite chemistry. Connolly et al., Biochemistry 23: 3443 (1984), discloses synthesis of oligonucleotide phosphorothioates using phosphoramidite chemistry. Jager el al., Biochemistry 27: 7237 (1988), discloses synthesis of oligonucleotide phosphoramidates using phosphoramidite chemistry. Solid phase synthesis of oligonucleotides by the phosphoramidite approach can be varied for different applications, but ordinarily involves the same generalized protocol. Briefly, this approach comprises anchoring the 3'-most nucleoside to a solid support functionalized with amino and/or hydroxyl moieties and subsequently adding the additional nucleosides in stepwise fashion. Desired internucleoside linkages are formed between the 3' phosphoramidite group of the incoming nucleoside and the 5' hydroxyl group of the 5'-most nucleoside of the nascent, support-bound oligonucleotide.

Refinement of methodologies is still required, however, particularly when making a transition to large-scale synthesis (10 umol to 1 mmol and higher). See Padmapriya et al., Antisense Res. Dev. 4: 185 (1994). Several modifications of the standard phosphoramidite methods have already been reported to facilitate the synthesis and isolation of oligonucleotides. See e.g., Padmapriya et al., supra; Ravikumar et al., Tetrahedron 50: 9255 (1994); Theisen et al., Nucleosides & Nucleotides 12: 43 (1994); and Iyer et al., Nucleosides & Nucleotides 14: 1349 (1995) (Kuijpers et al., Nucl. Acids Res. 18: 5197 (1990); and Reddy et al., Tetrahedron Lett. 35: 4311 (1994).

A major limiting factor for cost efficient synthesis of oligonucleotides is the time and cost required to make and purify the monomeric nucleoside phosphoramidites. Bodepudi et al., Chem. Res. Toxicol. 5: 608–617, discloses that the preparation of phosphoramidites from 2'-deoxy-7,8-dihydro-8-oxoguanosine and 2'-deoxy-7,8-dihydro-8-oxoadenosine according to the standard procedure results in extensive decomposition of the phosphoramidites during purification due to their instability and sensitivity to water. One potential approach to overcome these problems is to generate the phosphoramidite in situ as the oligonucleotide synthesis process is being carried out. Unfortunately, the numerous attempts at this approach have been disappointing. Moore and Beaucage, J. Org. Chem. 50: 2019–2025 (1985) teaches in situ preparation of phosphoramidites by reacting deoxyribonucleosides with bis-(pyrrolidino) methoxyphosphine activated by 4,5-dichloroimidazole in 1-methyl-2-pyrrolidinone. However, this method was limited by poor chemoselectivity, with about 8–10% (3'-3')-dinucleoside methyl phosphite triester being formed as a by-product. Barone et al., Nucleic Acids Res. 12: 4051–4061 (1984) and Lee and Moon, Chem. Lett. 1229–1232 (1984) disclose better chemoselectivity in preparation of phosphoramidites in situ, by reacting deoxyribonucleosides with bis-(N,N,-dialkylamino)alkoxyphosphines and 1H-tetrazole or its N,N-diisopropylammonium salt. Unfortunately, the tetrazole-N,N-diisopropylammonium salt, either added or generated in situ may form precipitates inside the synthesizer. Helinski et al., Tetrahedron Lett. 32: 4981–4984 (1991) and 34: 6451–6454 (1993) disclose selective activation of bifunctional phosphitylating reagents containing a p-nitrophenoxy group. However, this methodology is not adaptable in current phosphoramidite approaches because the p-nitrophenoxy group has to be activated by using a strong base. Finally, Fourrey et al., Tetrahedron Lett. 22: 729–732 (1981) and Cao et al., Tetrahedron Lett. 24: 1019–1020 (1983) disclose, as reactive bifunctional phosphitylating agents, phosphorodichlorite and the corresponding ditetrazolite and ditriazolite. Unfortunately, the application of these agents to the synthesis of oligonucleotides is generally problematic, because of their extremely high reactivity and poor chemoselectivity.

There is, therefore, a need for new bifunctional phosphitylating reagents and their application in in situ preparation of 5'-protected nucleoside phosphoramidites and synthesis of oligonucleotides without prior purification of the nucleoside phosphoramidites. Ideally, such reagents should react quickly with nucleosides under neutral or weakly basic conditions, without an additional activation step, should generate chemoselectively the corresponding nucleoside phosphoramidites in situ, and should be relatively stable and easy to handle.

BRIEF SUMMARY OF THE INVENTION

The invention provides novel bifunctional phosphitylating reagents and their application in in situ preparation of 5'-protected nucleoside phosphoramidites and synthesis of oligonucleotides. Bifunctional phosphitylating reagents according to the invention react quickly with nucleosides under neutral or weakly basic conditions, without an additional activation step. In addition, the bifunctional phosphitylating reagents according to the invention generate chemoselectively the corresponding nucleoside phosphoramidites in situ, without the need to purify the nucleoside phosphoramidites before using them in oligonucleotide synthesis. Finally, the bifunctional phosphitylating reagents according to the invention are relatively stable and easy to handle.

In a first aspect, the invention provides bifunctional phosphitylating reagents which are useful for in situ preparation of 5'-protected nucleoside phosphoramidites and synthesis of oligonucleotides. Bifunctional phosphitylating reagents according to the invention have the general structure (I):

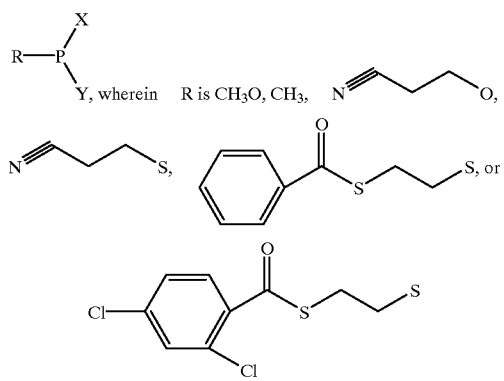

wherein the right-most O, C, or S is the point of attachment to phosphorous;

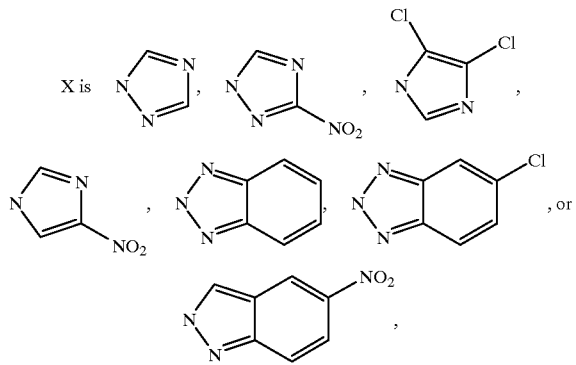

wherein the left-most N is the point of attachment to phosphorous;

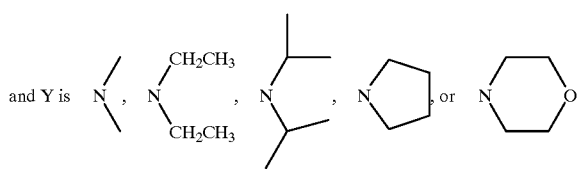

wherein the left-most N is the point of attachment to phosphorous. Bifunctional phosphitylating reagents according to the invention react in the presence of a secondary or tertiary amine with 5'-protected nucleosides to chemoselectively produce 5'-protected nucleoside-3'-phosphoramidites.

In a second aspect, the invention provides a process for generating 5'-protected nucleoside phosphoramidites in situ, without producing a precipitate and without requiring purification of the nucleoside phosphoramidites prior to their use in oligonucleotide synthesis. In the process according to this aspect of the invention, bifunctional phosphitylating reagents according to the invention are reacted with 5'-protected nucleosides in the presence of a secondary or tertiary amine to produce a 5'-protected nucleoside phosphoramidite.

In a third aspect, the invention provides an improved process for synthesizing an oligonucleotide. In the process according to this aspect of the invention, the improvement comprises the step of generating the nucleoside phosphoramidite in situ, rather than adding purified nucleoside phosphoramidites at the appropriate point in a conventional oligonucleotide synthesis procedure.

The reagents and processes according to the invention are useful for producing a wide variety of unmodified or chemically modified oligonucleotide compounds, or radiolabeled oligonucleotide compounds, all of which are referred to herein generally as "oligonucleotides". The reagents and processes according to the invention can be used or practiced on a scale ranging from a small laboratory scale to a large commercial scale.

BRIEF DESCRIPTION OF THE DRAWINGS

FIG. 2 shows a scheme for in situ preparation a 5'-protected nucleoside phosphoramidite and its incorporation into a growing oligonucleotide chain.

DETAILED DESCRIPTION OF THE PREFERRED EMBODIMENTS

The invention relates to the chemical synthesis of oligonucleotides and to chemical entities useful in such synthesis. The patents and publications identified in this specification are within the knowledge of those skilled in this field and are hereby incorporated by reference in their entirety.

The invention provides novel bifunctional phosphitylating reagents and their application in in situ preparation of 5'-protected nucleoside phosphoramidites and synthesis of oligonucleotides. Bifunctional phosphitylating reagents according to the invention react quickly with nucleosides under neutral or weakly basic conditions, without an additional activation step. Bifunctional phosphitylating reagents according to the invention generate chemoselectively the corresponding nucleoside phosphoramidites in situ, without the need to purify the nucleoside phosphoramidites before using them in oligonucleotide synthesis. Finally, the bifunctional phosphitylating reagents according to the invention are relatively stable and easy to handle.

In a first aspect, the invention provides bifunctional phosphitylating reagents which are useful for in situ preparation of 5'-protected nucleoside phosphoramidites and synthesis of oligonucleotides. Bifunctional phosphitylating reagents according to the invention have the general structure (I):

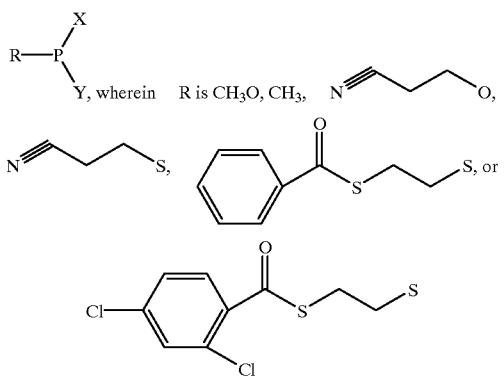

wherein the right-most O, C, or S is the point of attachment to phosphorous;

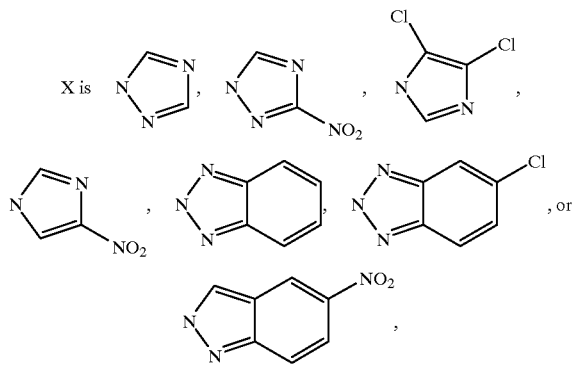

wherein the left-most N is the point of attachment to phosphorous;

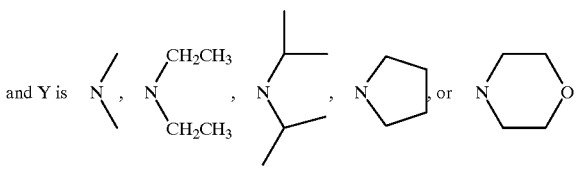

wherein the left-most N is the point of attachment to phosphorous. Bifunctional phosphitylating reagents according to the invention react in the presence of a secondary or tertiary amine with 5'-protected nucleosides to chemoselectively produce 5'-protected nucleoside-3'-phosphoramidites.

Figure 1:
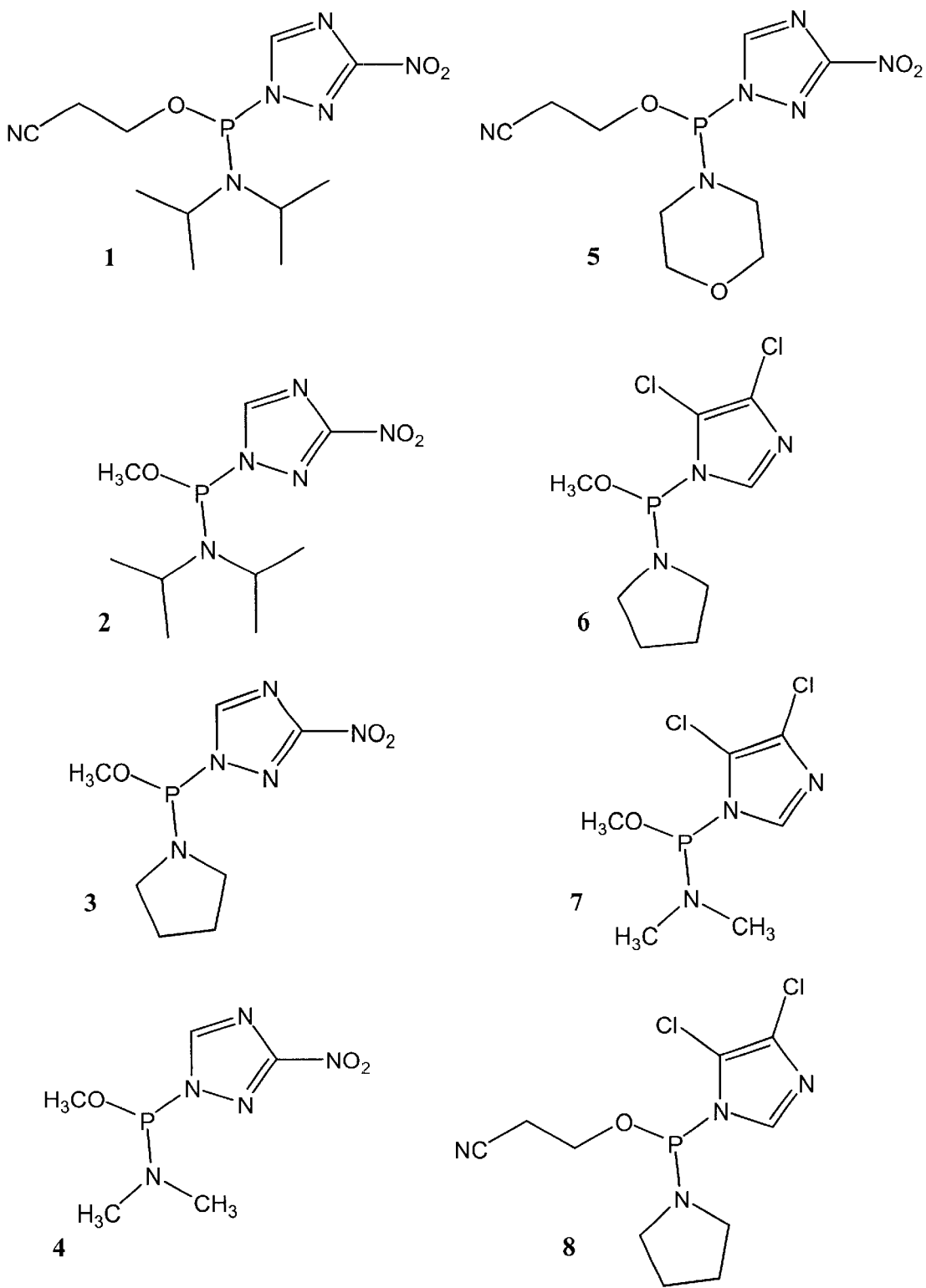
FIG. 1 shows eight particularly preferred embodiments of bifunctional phosphitylating reagents according to the invention.

Particularly preferred embodiments of bifunctional phosphitylating reagents according to the invention are shown in FIG. 1. Each of these particularly preferred embodiments has a high reactivity to 5'-protected nucleosides and can be selectively activated in the presence of a secondary or tertiary amine to form 5'-protected nucleoside phosphoramidites. One particularly preferred bifunctional phosphitylating reagent according to the invention is 2-cyanoethoxy (N,N-diisopropylamino) 3-nitro-1,2,4-triazolylphosphine, which is shown as compound 1 in FIG. 1. It is a pale yellow wax-like solid and is quite stable at both −20° C. and room temperature.

Figure 3:
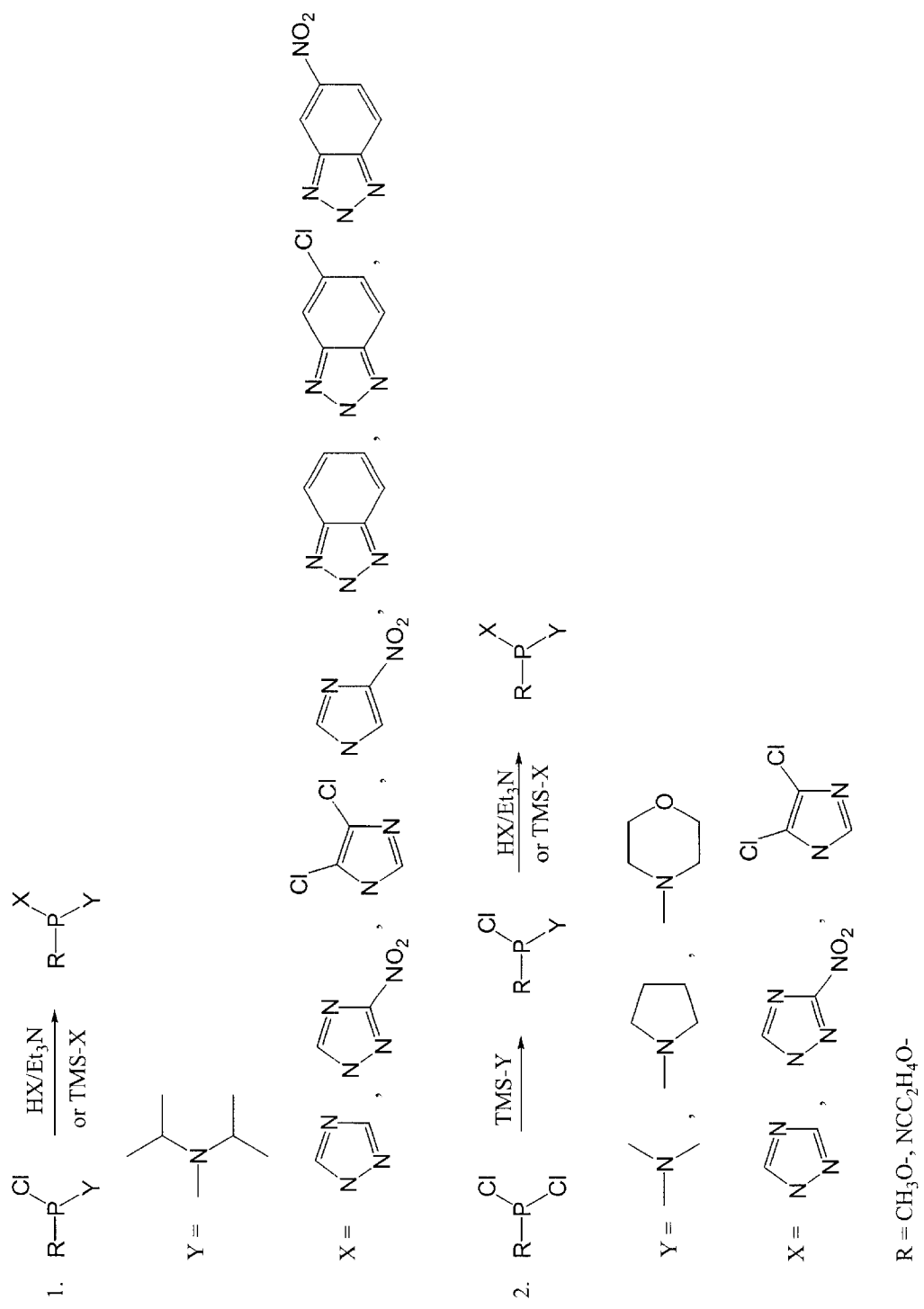
FIG. 3 shows two schemes for synthesizing bifunctional phosphitylating reagents according to the invention.
Figure 4:
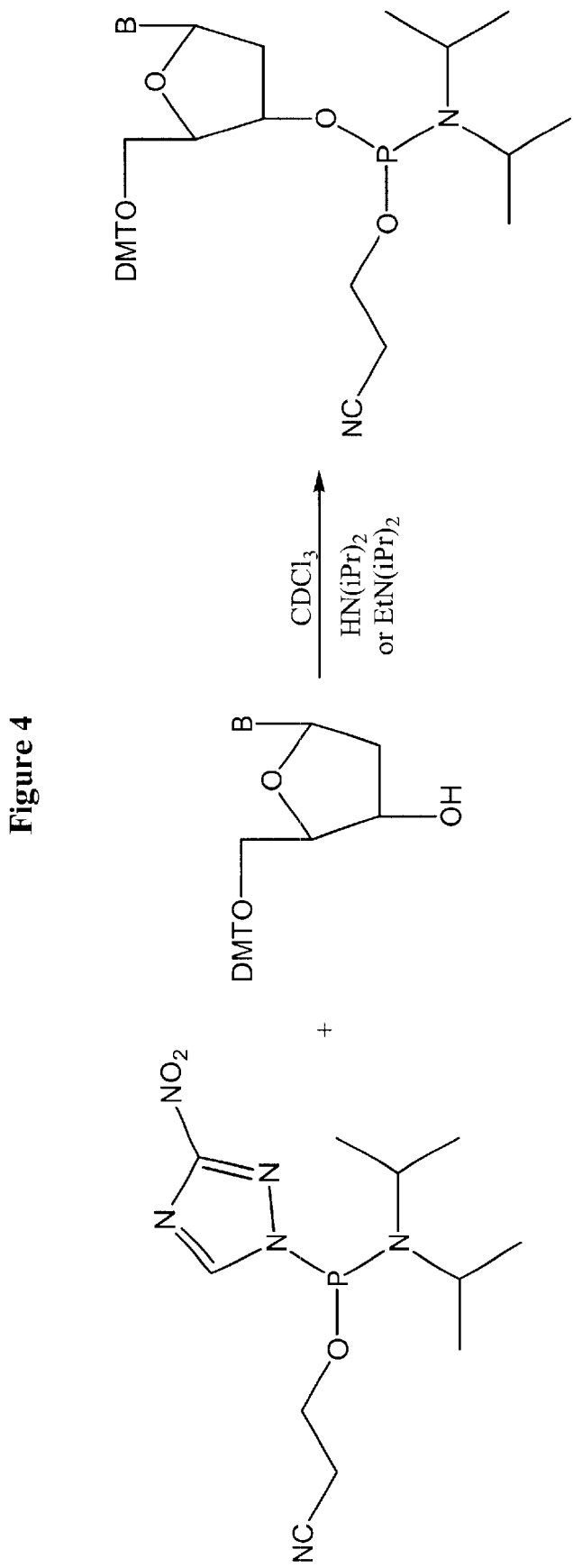
FIG. 4 shows a scheme for in situ preparation of a 5'-DMT nucleoside phosphoramidite using a particularly preferred bifunctional phosphitylating reagent according to the invention.

Bifunctional phosphitylating reagents according to the invention can be synthesized according to either of the schemes shown in FIG. 3. Compounds having a diisopropylamino group at the Y position (e.g., compounds 1 and 2 in FIG. 1) can be prepared from alkoxy(chloro)-N,N-diisopropylamino-phosphine and the appropriate heterocycle in the presence of triethylamine (upper scheme). Alternatively, these compounds can be prepared from alkoxy(chloro)-N,N-diisopropylamino-phosphine and the trimethylsilyl (TMS) derivative of the appropriate heterocycle (lower scheme). Compounds having a dimethylamino, morpholino, or pyrrolidino group at the Y position (e.g., compounds 3–8 in FIG. 1) can be synthesized by reacting alkoxydichlorophosphine with an appropriate (dialkylamino) trimethylsilane, followed by reaction with an appropriate heterocycle, either in the presence of triethylamine or by using the TMS derivative of the heterocycle.

In a second aspect, the invention provides processes for generating 5'-protected nucleoside phosphoramidites in situ, without producing a precipitate and without requiring purification of the nucleoside phosphoramidites prior to their use in oligonucleotide synthesis. In the process according to this aspect of the invention, bifunctional phosphitylating reagents according to the invention are reacted with 5'-protected nucleosides in the presence of a secondary or tertiary amine to produce a 5'-protected nucleoside phosphoramidite. Appropriate 5'-protected nucleosides include adenosine, guanosine, cytosine, uridine, inosine and thymidine, as well as modified nucleosides (see e.g., Sanghvi, in *Antisense Research and Applications*, pp. 273–288 (Crook and Lebleu, Eds.) CRC Press (1993) and the references cited therein). The 5' position of the nucleoside may be protected by any of the standard protecting groups (see e.g., Sonveaux in *Protocols for Oligonucleotide Conjuqates*, pp. 1–72 (S. Agrawal, Ed.), Humana Press (1994)) or with any protective group suitable for oligonucleotide synthesis. In certain preferred embodiments, the 5' position of the nucleoside is protected by a dimethoxytrityl (DMT) group.

For purposes of the invention, the term in situ is intended to mean "without intervening purification". Thus, generating 5'-protected nucleoside phosphoramidites in situ takes place whenever at least one of the 5'-protected nucleoside phosphoramidites are generated and then used for oligonucleotide synthesis without intervening purification of the 5'-protected nucleoside phosphoramidites. Such generation of the 5'-protected nucleoside phosphoramidites and synthesis of oligonucleotides may take place in the same reaction vessel or in different reaction vessels. Moreover, the generation of 5'-protected nucleoside phosphoramidites may take place either prior to, or contemporaneous with oligonucleotide synthesis.

The reaction between the bifunctional phosphitylation reagent and the 5'-protected nucleoside can be monitored by conventional $^{31}$p NMR spectroscopy. The most preferred bifunctional phosphitylation reagents according to the invention will react to completion with the 5'-protected nucleoside within about 10 minutes. The exact reaction rate will vary with the nature of the N,N-dialkylamino and/or the alkyl, O-alkyl, O- or S-cyanoethyl, or other R groups.

When bifunctional phosphitylating reagents according to the invention are used in the process according to this aspect of the invention, to obtain chemoselectivity of the reaction for the desired 5'-protected nucleoside phosphoramidite, the reaction is preferably carried out in the presence of a secondary or tertiary amine. Otherwise, a 3'—3' nucleoside dimer may under certain circumstances be obtained as a by-product. This is because the reaction between the phosphitylating reagent and the 5'-protected nucleoside produces both the 5'-protected nucleoside phosphoramidite and a released heterocycle molecule. In cases in which the released heterocycle is a weak acid, it can activate the dialkylamino group on the 5'-protected nucleoside phosphoramidite, which can then react with a 5'-protected nucleoside to produce the dimer. Secondary or tertiary amines can avoid this side reaction by trapping the released heterocycle. Preferably, this can be accomplished by carrying out the reaction between the phosphitylation reagent and the 5'-protected nucleoside in the presence of diisopropylethylamine or diisopropylamine, most preferably in the presence of about one equivalent of either or both.

In a third aspect, the invention provides an improved process for synthesizing an oligonucleotide. In the process according to this aspect of the invention, the improvement comprises the step of generating the nucleoside phosphoramidite in situ, rather than adding purified nucleoside phosphoramidites at the coupling step in a conventional oligonucleotide synthesis procedure.

The improvement according to this aspect of the invention can be incorporated into any standard phosphoramidite synthesis protocol using any automated synthesizer. For example, for small scale oligonucleotide synthesis, a standard protocol for oligonucleotide synthesis on a 0.2 or 1.0 micromole scale using a Millipore 8909 Expedite™ automated synthesizer (Millipore, Bedford, Mass.) can be followed, except that at the points at which 5'-protected nucleoside phosphoramidites are normally added, instead, a 0.1 M solution of 5'-protected nucleoside phosphoramidite is generated in situ, by adding to the reaction a bifunctional phosphitylating reagent according to the invention and a 5'-protected nucleoside in the presence of one equivalent of a secondary or tertiary amine, such as diisopropylethylamine or diisopropylamine. This procedure produces oligonucleotides in an average stepwise yield of >98%. For larger scale synthesis, similar modification of a large scale synthesis procedure can be carried out, by using a proportionately larger amount of bifunctional phosphitylating reagent and 5'-protected nucleoside.

The versatility of the improvement according to this aspect of the invention allows it to be used for the synthesis of a wide variety of different oligonucleotides. For purposes of the invention, the term "oligonucleotide" includes polymers of two or more deoxyribonucleotide or 2'-O-substituted ribonucleotide monomers, or any combination thereof. Such monomers may be coupled to each other by any of the numerous known internucleoside linkages. In certain preferred embodiments, these internucleoside linkages may be phosphodiester, phosphotriester, phosphorothioate, phosphorodithioate, methylphosphonate, or phosphoramidate linkages, or combinations thereof. The term oligonucleotide also encompasses such polymers having chemically modified or radioisotopically labeled bases or sugars and/or having additional substituents, including without limitation lipophilic groups, intercalating agents, diamines and adamantane. For purposes of the invention the term "2'-O-substituted" means substitution of the 2' position of the pentose moiety with an —O—alkyl group containing 1–6 saturated or unsaturated carbon atoms, or with an —O—aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carbalkoxyl, or amino groups; or such 2' substitution may be with a hydroxy group (to produce a ribonucleoside), an amino or a halo group, but not with a 2'-H group.

The following examples are intended to further illustrate certain preferred embodiments of the invention and are not intended to be limiting in nature. Except as otherwise indicated, in each of the following examples, anhydrous acetonitrile, tetrahydrofuran, dichloromethane were purchased from Aldrich (Milwaukee, Wis.). Triethylamine, diisopropylamine and diisopropylethylamine were also purchased from Aldrich, and distilled from calcium hydride before use. Anhydrous acetonitrile were purchased from J. T. Baker Inc. (Phillipsburg, N.J.). dT-CPG, 5'-DMT-deoxyadenosine (Bz) cyanoethyl phosphoramidite, 5'-DMT-deoxycytidine (Bz) cyanoethyl phosphoramidite, 5'-DMT-deoxyguanosine (ibu) Cyanoethyl phosphoramidite, 5'-DMT-thymidine Cyanoethyl phosphoramidite, Cap A, Cap B, activator, oxidizing and deblock solutions were purchased from PerSeptive Biosystems, (Framingham, Mass.). Beaucage reagent (3H-1,2-benzodithiol-3-one-1,1-dioxide) was purchased from R. I. Chemical (Orange, Calif.). All other chemicals were purchased from Aldrich. $^{31}$P NMR spectra (121.65 MHz) and $^1$H NMR spectra (300 MHz) were recorded on a Varian UNITY 300 (the chemical shift was correlated to 85% $H_3PO_4$ and tetramethylsilane, respectively). Oligonucleotide synthesis was performed on a 8909 Expedite™ DNA synthesizer (Millipore). Compound numbers, shown in bold, refer to the compounds shown in FIG. 1.

EXAMPLE 1

Synthesis of Chloro(N,N-dimethylamino) methoxyphosphine

To a solution of methyldichlorophosphite (10.0 g, 75.24 mmol, 7.1 mL) in $CH_2Cl_2$ (50 mL) was added dropwise N,N-dimethyltrimethylsilylamine (12.1 mL, 8.8 g, 75.2 mmol) at 0° C. the resulting mixture was stirred for 2 h at room temperature. The solvent was removed under reduced pressure to give a colorless oil (10.33 g, 97%) as a product. $^1$H NMR (CDCl$_3$) δ 3.64 (d, J=13.5 Hz, 3H), 2.66 (s, 3H), 2.62 (s, 3H); $^{31}$P NMR (CDCl$_3$) δ 179.4.

EXAMPLE 2

Synthesis of Chloro(methoxy)pyrrolidinophosphine

To a solution of methyldichlorophosphite (10.0 g, 75.24 mmol, 7.1 mL) in $CH_2Cl_2$ (50 mL) was added dropwise 1-(trimethylsilyl)pyrrolidine (13.1 mL, 10.8 g, 75.2 mmol) at 0° C. The resulting mixture was stirred for 2 h at room temperature. The solvent was removed under reduced pressure to give a colorless oil (11.97 g, 95%) as a product. $^{31}$P NMR (CDCl$_3$) δ 182.3.

EXAMPLE 3

Synthesis of Chloro(2-Cyanoethoxy) morpholinophosphine

To a solution of 2-Cyanoethyldichlorophosphite (3.0 g, 17.5 mmol, 2.2 mL) in $CH_2Cl_2$ (45 mL) was added dropwise 4-(trimethylsilyl)morpholine (3.1 mL, 2.8 g, 17.5 mmol) at 0° C. The resulting mixture was stirred for 2 h at room temperature. The solvent was removed under reduced pressure to give a pale yellow oil (3.87 g, 86%) as a product.

EXAMPLE 4

Synthesis of Chloro(2-Cyanoethyoxy) pyrrolidinophosphine

To a solution of 2-Cyanoethyldichlorophosphite (2.0 g, 11.6 mmol, 1.5 mL) in $CH_2Cl_2$ (30 mL) was added dropwise 4-(trimethylsilyl)pyrrolidine (2.0 mL, 1.7 g, 11.6 mmol) at 0° C. The resulting mixture was stirred overnight at room temperature. The solvent was removed under the reduced pressure to give a colorless oil (2.48 g, 88%) as a product.

EXAMPLE 5

Synthesis of 2-Cyanoethoxy(N,N-diisopropylamino)(3-nitro-1,2,4-triazolyl)phosphine (1)

To a stirred solution of 3-nitro-1,2,4-triazole (9.64 g, 84.50 mmol) and triethylamine (14.0 mL, 10.26 g, 101.4 mmol) in THF (200 mL) was added dropwise chloro-2-cyanoethoxy-N,N-diisopropylaminophosphine (20.0 g, 84.50 mmol) at room temperature. The mixture was stirred overnight at room temperature. The reaction mixture was filtered to remove the resulting salt, and the solvent was removed under reduced pressure to give the crude product as a pale brown oil (24.9 g, 95%). After standing at room temperature, the oil becomes a pale yellow wax-like solid. $^1$H NMR (CDCl$_3$ δ 8.39 (s, 1H), 4.09 (m, 2H), 3.51 (m, 2H), 2.81 (m, 2H), 1.19 (d, J=6.0 Hz, 6H), 1.07 (d, J=9.0 Hz, 6H). $^{31}$P NMR (CDCl$_3$) δ 133.9.

EXAMPLE 6

Synthesis of Methoxy-N,N-diisopropylamino(3-nitro-1,2,4-triazolyl)phosphine (2)

To a stirred solution of 3-nitro-1,2,4-triazole (0.69 g, 6.07 mmol) and triethylamine (2.82 mL, 2.05 g, 20.2 mmol) in THF (10 mL) and CH$_2$Cl$_2$ (20 mL) was added dropwise chloro(N,N-diisopropylamino)methoxyphosphine (1.0 g, 5.06 mmol) at room temperature. The mixture was stirred overnight at room temperature. The reaction mixture was filtered to removed the resulting salt, and the solvent was removed under reduced pressure to give the crude product as a pale brown oil (1.24 g, 89%). $^{31}$P NMR (CDCl$_3$) δ 135.9.

EXAMPLE 7

Synthesis of Methoxy(3-nitro-1,2,4-triazolyl)pyrrolidinophosphine (3)

To a stirred solution of 3-nitro-1,2,4-triazole (2.70 g, 23.71 mmol) and triethylamine (11.0 mL, 8.0 g, 79.0 mmol) in THF (40 mL) and CH$_2$Cl$_2$ (20 mL) was added dropwise chloro(methoxy)pyrrolidinophosphine (3.31 g, 19.76 mmol) at room temperature. The mixture was stirred overnight at room temperature. The reaction mixture was filtered to remove the resulting salt, and the solvent was removed under reduced pressure to give the crude product as a pale yellow oil (3.97 g, 82%). $^{31}$P NMR (CDCl$_3$) δ 132.9.

EXAMPLE 8

Synthesis of N,N-Dimethylamino(Methoxy)(3-nitro-1,2,4-triazolyl)phosphine (4)

To a stirred solution of 3-nitro-1,2,4-triazole (2.86 g, 25.1 mmol) and triethylamine (14.0 mL, 10.2 g, 101 mmol) in THF (40 mL) was added dropwise Chloro(N,N-dimethylamino)methoxyphosphine (3.55 g, 25.1 mmol) in CH$_2$Cl$_2$ (10 mL) at room temperature. The mixture was stirred for 3 h at room temperature. The reaction mixture was filtered to remove the resulting salt, and the solvent was removed under reduced pressure to give the crude product as a yellow oil (4.56 g, 83%) $^{31}$P NMR (CDCl$_3$) δ 134.9.

EXAMPLE 9

Synthesis of 2-Cyanoethoxy(3-nitro-1,2,4-triazolyl)mopholinophosphine (5)

To a stirred solution of 3-nitro-1,2,4-triazole (2.57 g, 22.57 mmol) and triethylamine (12.58 mL, 9.14 g, 90.28 mmol) in CH$_2$Cl$_2$ (40 mL) was added dropwise Chloro(2-Cyanoethoxy)morpholinophosphine (5.82 g, 22.57 mmol) at room temperature. The mixture was stirred overnight at room temperature. The reaction mixture was filtered to remove the resulting salt, and the solvent was removed under reduced pressure to give the crude product as a yellow oil (5.98 g, 79%). $^{31}$P NMR (CDCl$_3$) δ 126.9.

EXAMPLE 10

Synthesis of 4,5-dichloroimidazolyl(Methoxy)pyrrolidinophosphine (6)

To a stirred solution of 4,5-dichloroimidazole (4.62 g, 33.7 mmol) and triethylamine (18.8 mL, 13.65 g, 134.9 mmol) in THF (40 mL) was added dropwise Chloro(methoxy)pyrrolidinophosphine (3.31 g, 19.76 mmol) CH$_2$Cl$_2$ (13.4 mL) at room temperature. The mixture was stirred for 3 h at room temperature. The reaction mixture was filtered to remove the resulting salt, and the solvent was removed under reduced pressure to give the crude product as a pale yellow oil (7.76 g, 86%). $^{31}$P NMR (CDCl$_3$) δ 125.9.

EXAMPLE 11

Synthesis of 4,5-dichloroimidazolyl-N,N-Dimethylamino(Methoxy)phosphine (7)

To a stirred solution of 4,5-dichloroimidazole (3.44 g, 25.1 mmol) and triethylamine (14.0 mL, 10.16 g, 100.4 mmol) in THF (30 mL) was added dropwise Chloro(N,N-dimethylamino)methoxyphosphine (3.55 g, 25.1 mmol) in CH$_2$Cl$_2$ (10 mL) at room temperature. The mixture was stirred for 2 h at room temperature. The reaction mixture was filtered to remove the resulting salt, and the solvent was removed under reduced pressure to give the crude product as a yellow oil (2.81 g, 79%). $^{31}$P NMR (CDCl$_3$) δ 129.3.

EXAMPLE 12

Synthesis of 2-Cyanoethoxy(4,5-dichloroimidazolyl)pyrrolidinophosphine (8)

To a stirred solution of 4,5-dichloroimidazole (1.59 g, 11.63 mmol) and triethylamine (1.95 mL, 1.41 g, 13.96 mmol) in CH$_2$Cl$_2$ (30 mL) was added dropwise Chloro(2-Cyanoethoxy) pyrrolidinophosphine (2.40 g, 11.63 mmol) in CH$_2$Cl$_2$ (10 mL) at room temperature. The mixture was stirred for 4 h at room temperature. The reaction mixture was filtered to remove the resulting salt, and the solvent was removed under reduced pressure to give the crude product as a pale yellow oil (2.93 g, 82%). $^{31}$P NMR (CDCl$_3$) δ 123.2.

EXAMPLE 13

In Situ Preparation of 5'-DMT-Thymidine CED Phosphoramidites

To 1.65 mmol (0.90 g) of 5'-DMT-thymidine in THF (8.3 mL) was added a solution of 1 (0.54 g, 1.73 mmol) and N,N-diisopropylethylamine (0.31 mL, 0.23 g, 1.78 mmol) in CH$_3$CN (8.3 mL) at room temperature. The mixture was stirred for 5 min and the phosphoramidite solution (0.1 M) was ready to use.

EXAMPLE 14

In Situ Preparation of N$^2$-iBu-5-DMT-2-deoxyGuanosine CED Phosphoramidites

To 2.0 mmol (1.28 g) of 5'-DMT-dG$^{iBu}$ in THF (10.0 mL) was added a solution of 1 (0.66 g, 2.1 mmol) and N,N- diisopropylethylamine (0.38 mL, 0.28 g, 2.2 mmol) in CH$_3$CN (10.0 mL) at room temperature. The mixture was stirred for 5 min and the phosphoramidite solution (0.1 M) was ready to use.

EXAMPLE 15

In Situ Preparation of N$^6$-Bz-5-DMT-2-deoxyAdenosine CED Phosphoramidites

To 2.0 mmol (1.32 g) of 5'-DMT-dA$^{Bz}$ in THF (10.0 mL) was added a solution of 1 (0.66 g, 2.1 mmol) and N,N-diisopropylethylamine (0.38 mL, 0.28 g, 2.2 mmol) in CH$_3$CN (10.0 mL) at room temperature. The mixture was stirred for 5 min and the phosphoramidite solution (0.1 M) was ready to use.

EXAMPLE 16

In Situ Preparation of N$^4$-Bz-5'-DMT-2'-deoxyCytidine CED Phosphoramidites

To 2.0 mmol (1.27 g) of 5'-DMT-dC$^{Bz}$ in CH$_3$CN (10.0 mL) was added a solution of 1 (0.66 g, 2.1 mmol) and N,N-diisopropylethylamine (0.38 mL, 0.28 g, 2.2 mmol) in CH$_3$CN (10.0 mL) at room temperature. The mixture was stirred for 5 min and the phosphoramidite solution (0.1 M) as ready to use.

EXAMPLE 17

$^{31}$P NMR Spectroscopy Analysis of Nucleoside Phosphoramidite Monomers

To 0.20 mmol of 1 (62.79 mg) was added a solution of 5'-DMT-thymidine (92.4 mg, 0.17 mmol) and N,N,-diisopropylethylamine (0.035 mL, 25.9 mg, 0.20 mmol) in CDCl$_3$ (0.7 mL) at room temperature. After stirring for 10 min. at room temperature, the solution was transferred into an NMR tube and examined by conventional NMR spectroscopy. The results showed 98% of the product to be the expected nucleoside phosphoramidite product. Similar results were obtained using each of the reagents 2–8.

EXAMPLE 18

Synthesis of Oligonucleotides

The oligonucleotide phosphorothioate and phosphodiester were synthesized on a 0.2 and 1 micromole scale following the standard protocol using an automated synthesizer (Millipore 8909 Expedite™, Bedford, Mass.) except that the step of adding nucleoside phosphoramidite was replaced by the in situ generation of the nucleoside phosphoramidite as described in Example 17. For oligonucleotide phosphorothioate, the iodine oxidation step was replaced by sulfurization with 3H-1,2-benzodithiol-3-one-1,1-dioxide (Beaucage reagent). Eight-hour treatment with ammonium hydroxide at 65° C. was carried out to cleave the oligomer from the support and to deprotect nucleoside bases. The mixture was filtered to remove the CPG. After the ammonium hydroxide solution was removed by Speed Vac, the remaining crude products were submitted to CE and IE-HPLC analysis.

What is claimed is:

1. A bifunctional phosphitylating reagent having the structure:

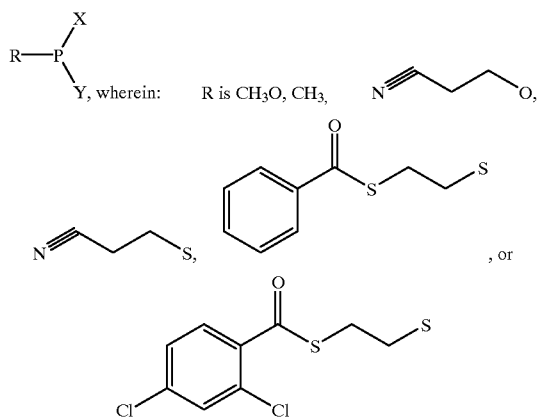

wherein the right-most O, C, or S is the point of attachment to phosphorous; X is

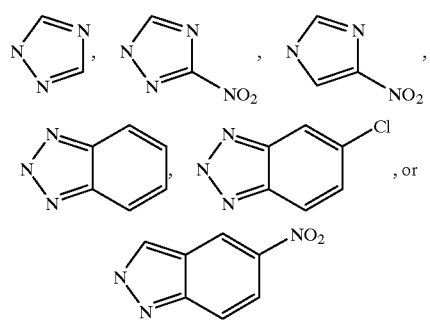

wherein the left-most N is the point of attachment to phosphorous; and Y is

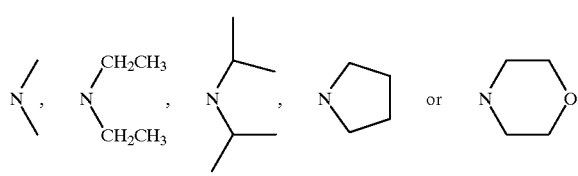

wherein the left-most N is the point of attachment to phosphorous.

2. The bifunctional phosphitylating reagent according to claim 1, wherein the reagent is selected from the group consisting of:

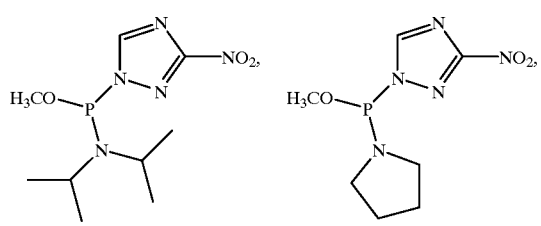

-continued

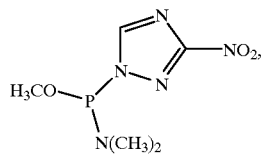

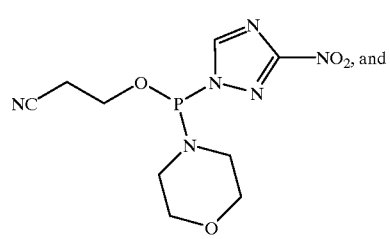

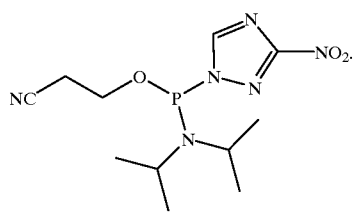

-continued

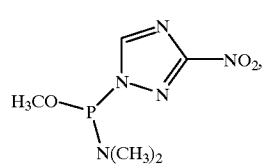

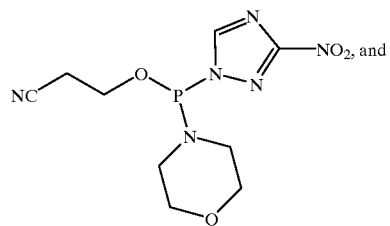

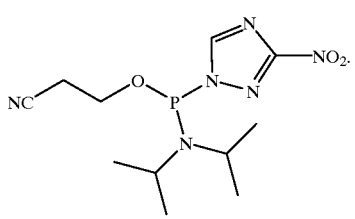

3. A process for generating 5'-protected nucleoside phosphoramidites in situ, the process comprising reacting a bifunctional phosphitylating reagent according to claim 1 with 5'-protected nucleosides in the presence of a secondary or tertiary amine to produce a 5'-protected nucleoside phosphoramidite.

4. The process according to claim 3, wherein the bifunctional phosphitylating reagent is selected from the group consisting of:

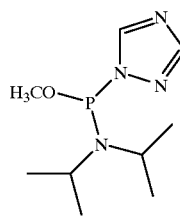 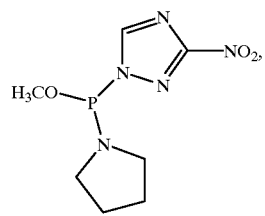

5. An improved process for synthesizing an oligonucleotide, the improvement comprising generating the nucleoside phosphoramidite in situ according to the process of claim 3.

6. An improved process for synthesizing an oligonucleotide, the improvement comprising generating the nucleoside phosphoramidite in situ according to the process of claim 4.

* * * * *

UNITED STATES PATENT AND TRADEMARK OFFICE
CERTIFICATE OF CORRECTION

PATENT NO. : 6,340,749
DATED : January 22, 2002
INVENTOR(S) : Zhaoda Zhang and Jin-Yan Tang Page 1 of 1

It is certified that error appears in the above-identified patent and that said Letters Patent is hereby corrected as shown below:

Title page,
Item [54], please add the words --IN SITU -- to the beginning of the title.

Signed and Sealed this

Seventh Day of May, 2002

Attest:

Attesting Officer

JAMES E. ROGAN
Director of the United States Patent and Trademark Office